United States Patent
Lee et al.

(10) Patent No.: US 7,806,689 B2
(45) Date of Patent: Oct. 5, 2010

(54) DISPOSABLE DENTAL PROPHYLAXIS INSTRUMENT CAPABLE OF DISCHARGING DENTIFRICE MATERIAL

(76) Inventors: Kwang S. Lee, 11731 Welebir St., Loma Linda, CA (US) 92354; Duke K. Ghim, 10720 Lakewood Blvd., #335, Downey, CA (US) 90241

( * ) Notice: Subject to any disclaimer, the term of this patent is extended or adjusted under 35 U.S.C. 154(b) by 0 days.

(21) Appl. No.: 12/342,081

(22) Filed: Dec. 23, 2008

(65) Prior Publication Data
US 2010/0159416 A1    Jun. 24, 2010

(51) Int. Cl.
*A61C 1/10*    (2006.01)
(52) U.S. Cl. .......................................... 433/82; 433/89
(58) Field of Classification Search .................. 433/80, 433/82, 83, 87, 89, 125; 15/24, 31; 222/101; 401/137, 138, 179
See application file for complete search history.

(56) References Cited

U.S. PATENT DOCUMENTS

| | | | |
|---|---|---|---|
| 2,400,912 A | 5/1946 | Britt et al. | |
| 2,738,528 A | 3/1956 | Fridge, Sr. | |
| 3,775,849 A | 12/1973 | Condon | |
| 3,987,550 A | 10/1976 | Danne | |
| 4,010,873 A * | 3/1977 | Mardirossian | 222/101 |
| 4,220,446 A | 9/1980 | Walker | |
| 4,266,933 A | 5/1981 | Warden | |
| 4,615,635 A * | 10/1986 | Kim | 401/270 |
| 5,062,796 A | 11/1991 | Rosenberg | |
| 5,638,840 A * | 6/1997 | Lee et al. | 132/310 |
| 5,642,994 A | 7/1997 | Chipian | |
| 6,257,886 B1 | 7/2001 | Warner | |
| 7,029,278 B2 | 4/2006 | Pond | |
| 2006/0127844 A1* | 6/2006 | Michaelian | 433/125 |

* cited by examiner

*Primary Examiner*—Cris L Rodriguez
*Assistant Examiner*—Eric Rosen
(74) *Attorney, Agent, or Firm*—Louis F. Teran

(57) ABSTRACT

The present invention relates to a disposable dental instrument used by dental professionals to polish a patient's teeth. The dental instrument can be connected to a hand motor used to rotate a prophy cup with a plurality of grinding wings that rub against the patient's teeth as a predetermined amount of tooth cleaning fluid is discharged directly on the patient's teeth through a drain hole within the prophy cup. The tooth cleaning fluid is discharged from a tube that is assembled in a tube room of the dental instrument. The tube is a flexible bladder similar in function and form to a tube of toothpaste. The tube is made of a flexible polymer material that allows it to be squeezed when pressure is applied to it. A roller is assembled within the tube room and on top of the tube. As the roller is pushed forward with a finger, the tube is squeezed to discharge the tooth cleaning fluid directly on the patient's teeth.

14 Claims, 12 Drawing Sheets

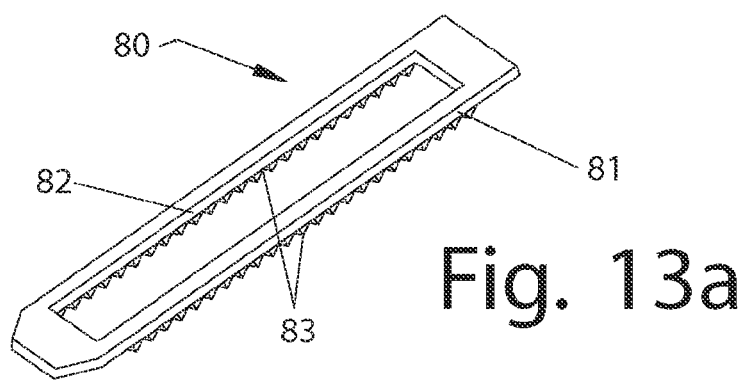
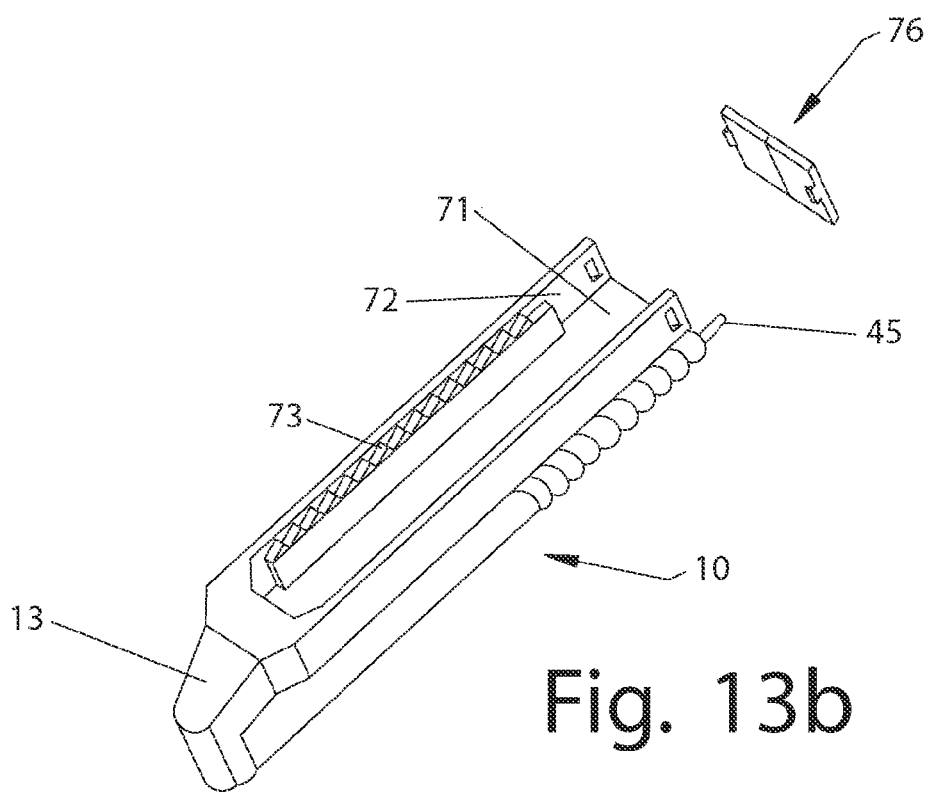

DISPOSABLE DENTAL PROPHYLAXIS INSTRUMENT CAPABLE OF DISCHARGING DENTIFRICE MATERIAL

BACKGROUND OF THE INVENTION

1. Field of the Invention

The present invention relates to a dental instrument adapted to dispense tooth cleaning fluid to a patient's teeth. More specifically, without removing the instrument from the patient's mouth, a tooth cleaning fluid, such as prophylactic paste, is dispensed from the manually controlled instrument to enable the application of the cleaning fluid directly on the patient's teeth while a prophy cup attached to the instrument rotates to clean or polish the surface of the teeth.

2. Description of the Prior Art

The application of tooth cleaning fluid, such as prophylactic paste, to a patient's teeth is a common step in the teeth cleaning process conducted by dentists, oral hygienists, and other dental professionals. Traditionally, a prophy cup attached to a dental instrument is removed from the patient's mouth and dipped into a prophylactic paste-filled container to fill the cup. The dental instrument is then placed in the patient's mouth so that the prophy cup filled with prophylactic paste is pressed against the patient's teeth. A pneumatic actuated mechanism that is connected to the dental instrument then powers the rotation of the prophy cup so that it cleans or polishes the patient's teeth. The paste is used rapidly, thus the instrument must often be withdrawn from the patient's mouth to refill the prophy cup.

Dental instruments that dispense tooth cleaning fluid to a patient's teeth are well known in the art. Such instruments generally include some type of fluid container with a mechanism that is actuated to deliver the tooth cleaning fluid from the container to the teeth and a prophy cup that is rotated by a pneumatic mechanism to which the instrument is connected. The prior art is typically represented by U.S. Pat. Nos. 5,642,994; 7,029,278; 4,266,933; 6,257,886; 2,738,528; 4,220,446; 5,062,796; 3,987,550; 3,775,849; and 2,400,912.

U.S. Pat. No. 2,738,528 shows a handpiece with a flexible tube bent so as to allow the cleaning fluid in a collapsible dispenser to be manually forced through a flexible tube and into a prophy cup. The tube is made of flexible material that makes it prone to kinking. The small size of the tube also results in increased flow resistance and loss of volume. In addition, the collapsible dispenser is anchored to the handpiece by a single strap that can be dislodged when the dispenser is emptying.

U.S. Pat. No. 5,642,994 illustrates a dental instrument with a soft-walled bladder that needs to be anchored to securing pins so that an ellipsoid roller with projections on opposite sides which fit into slots in the retaining walls can be pushed forward to squeeze the tooth cleaning fluid from the bladder and into the prophy cup. Anchoring the bladder to the securing pins is difficult and not effective at holding the bladder in place as the roller squeezes the fluid. Secondly, the roller has small spline on the side projections that are very difficult and expensive to manufacture and difficult for the operator to push since the bladder pushes upward against the roller. This dental instrument is also difficult to use because of the tight space that the roller must squeeze into after anchoring the bladder to the securing pins.

U.S. Pat. No. 4,220,446 requires a secondary pneumatic source for dispensing the cleaning fluid. Furthermore, the cleaning fluid is not dispensed into the prophy cup as desired by dentists, oral hygienists, and other dental professionals. Finally, the bulky design makes it difficult for the operator to insert the tool into a patient's mouth.

U.S. Pat. No. 6,257,886 shows a design where the cleaning fluid is in the same hollow cavity in the housing as the rotating shaft that drives the rotation of the prophy cup. The cleaning fluid has a tendency to stick to the rotating shaft resulting in a slower rotation of the prophy cup. As the rotation of the cup is slowed, it loses its friction function against a patient's tooth required for proper cleaning or polishing of tooth. Additionally, as the shaft rotates, it generates heat within the cleaning fluid that can lead to changes of the properties of the fluid.

U.S. Pat. No. 4,266,933 shows a design where a helical conveyor is rotated to push the cleaning fluid toward the prophy cup. The size of the helical conveyor makes the design too bulky to be easily inserted into a patient's mouth. In addition, the rotation of the helical conveyor generates heat within the cleaning fluid that can change its properties.

U.S. Pat. No. 7,029,278 illustrates a design that does not dispense the cleaning fluid into the prophy cup but adjacent to the prophy cup. Additionally, the plunger that pushes the cleaning fluid toward the prophy cup is not controlled manually by the operator but by a drive member.

U.S. Pat. Nos. 5,062,796, 3,987,550, 3,775,849, and 2,400,912 show designs that require major reconfigurations to the traditional system used. The designs tend to incorporate a pneumatic pressure system for driving the cleaning fluid from a container and into a prophy cup. The major drawback to such design is the retooling that dental instruments already installed would require. Some of these designs even include foot-pedals or other elaborate actuation and control means that unnecessarily complicate the system.

SUMMARY OF INVENTION

Accordingly, the present invention has been made to address all of the problems present in the prior art.

It is an object of the present invention to provide a dental instrument that discharges a tooth cleaning fluid, such as prophylactic paste, into a prophy cup and directly on a patient's teeth without requiring the operator, such as a dentist, oral hygienist, or other dental professional to remove the instrument form the inside of patient's mouth.

It is another object of this invention to provide simple manual dispensing of the tooth cleaning fluid with a finger in a manner that is comfortable and natural to the operator.

It is another object of this invention to provide a dental instrument that is disposable and compatible with existing hand motors used by dentists, oral hygienists, and other dental professionals.

It is another object of this invention to provide a container for the cleaning fluid that is disposable and easy to replace.

It is another object of this invention to provide a dental instrument that can be operated with one hand, activated to dispense cleaning fluid with a finger, and that is small enough to be used inside a patient's mouth without interfering with the viewing or physical access to the patient's mouth.

It is another object of this invention to provide a dental instrument that can be manufactured in great quantities and at inexpensive costs.

These and other objects are realized in a dental instrument adapted to allow the operator to manually dispense tooth cleaning fluid into a prophy cup and directly on the patient's teeth without having to remove the instrument from the patient's mouth and while the prophy cup rotates to clean or polish the surface of the patient's teeth. The release of the tooth cleaning fluid is manually controlled by the operator's finger through a roller located on the top face of the instrument. As the roller is pushed forward it squeezes a flexible container holding the tooth cleaning fluid. As the flexible container is squeezed by the roller, the tooth cleaning fluid is pushed through a dispensing orifice and into a prophy cup. As the prophy cup is filled with tooth cleaning fluid, it is rotated by a commonly used hand motor to which the dental instrument is connected. The dental instrument is disposable and compatible with existing hand motors used by dentists, oral hygienists, and other dental professionals. The overall size of the instrument is small enough to be used inside a patient's mouth without interfering with the viewing or physical access of the patient's mouth.

These and other objects, features, advantages, and alternative aspects of the present invention will become apparent to those skilled in the art from a consideration of the following detailed description taken in combination with the accompanying drawings.

DESCRIPTION OF THE DRAWINGS

The above and other objects, features and advantages of the present invention will be apparent from the following detailed description of the preferred embodiments of the invention in conjunction with the accompanying drawings, in which:

FIG. 4b is an enlarged sectional view showing the parts in a circle 'A' of FIG. 4a;

FIG. 9b is a one side view of the stop key of FIG. 9a;

FIG. 10b is an elevational partially rear view of the rear end of the dental instrument shown in FIG. 10a;

FIG. 13a is a perspective view of an alternative embodiment of the lid of the disposable dental instrument of the present invention;

FIG. 13b is a perspective view of an alternative embodiment of the housing of the disposable dental instrument of the present invention;

DETAILED DESCRIPTION OF THE INVENTION

Reference will now be made to the drawings in which the various elements of the present invention will be given numerical designations and in which the invention will be discussed so as to enable one skilled in the art to make and use the invention.

Figure 1A:
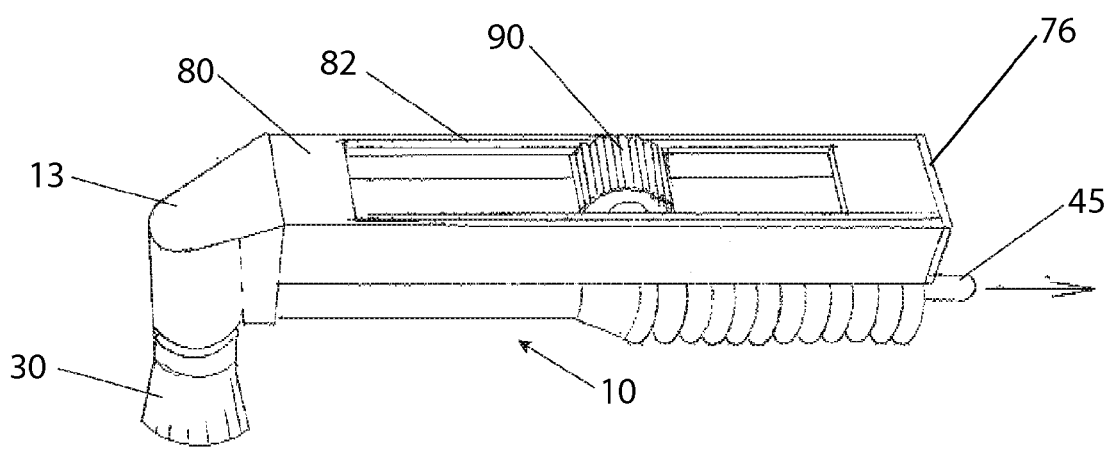
FIG. 1a is a perspective view showing a disposable dental instrument adapted to dispense tooth cleaning fluid to a patient's teeth according to the present invention.

FIG. 1a is a perspective view showing a disposable dental instrument adapted to dispense tooth cleaning fluid to a patient's teeth according to the present invention. It should be noted that while a tooth cleaning fluid is almost exclusively disclosed herein, other fluid-like substances may be stored and dispensed using the present invention. However, in a preferred embodiment, a tooth cleaning fluid most often referred to is a prophylactic paste, or prophy paste as it is commonly known.

Figure 1B:
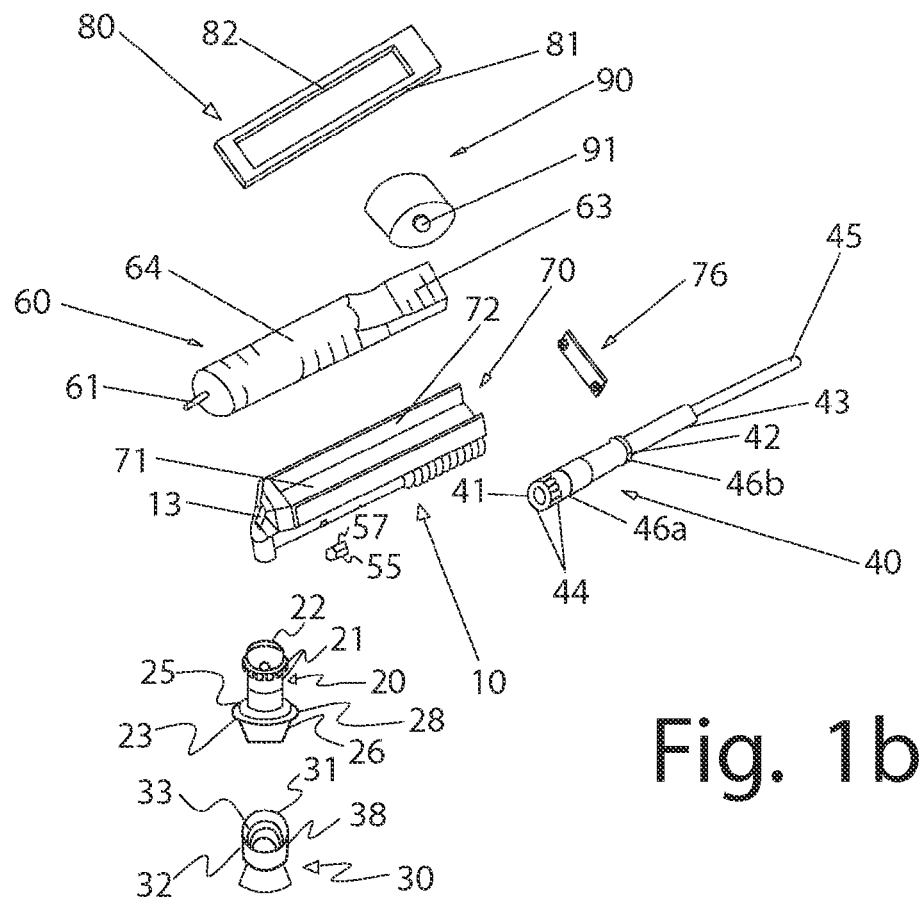
FIG. 1b is an exploded perspective view of the disposable dental instrument of the present invention.

FIG. 1b is an exploded perspective view showing a disposable dental instrument adapted to dispense tooth cleaning fluid to a patient's teeth according to the present invention. In more detail, the disposable dental instrument according to the present invention includes: a housing having a drain hole adapted for discharging a tooth cleaning fluid therefrom, a tube room adapted for mounting a tube filled with tooth cleaning fluid, a wheel room adapted for mounting a gear mechanism, and a central bore adapted for mounting a drive shaft that powers the rotation of a prophy cup; a wheel having a drain hole adapted for inducing the flow of the tooth cleaning fluid from the drain hole of the housing to the prophy cup adapted for rubbing against a patient's tooth; a prophy cup having a drain hole formed for receiving the tooth cleaning fluid induced from the drain hole of the wheel; a tube adapted to be charged with the tooth cleaning fluid and manufactured of a flexible polymer material; a roller adapted to squeeze the tooth cleaning fluid from the tube more efficiently and thoroughly than a finger; and a lid that attaches to the top of the tube room.

Figure 2:
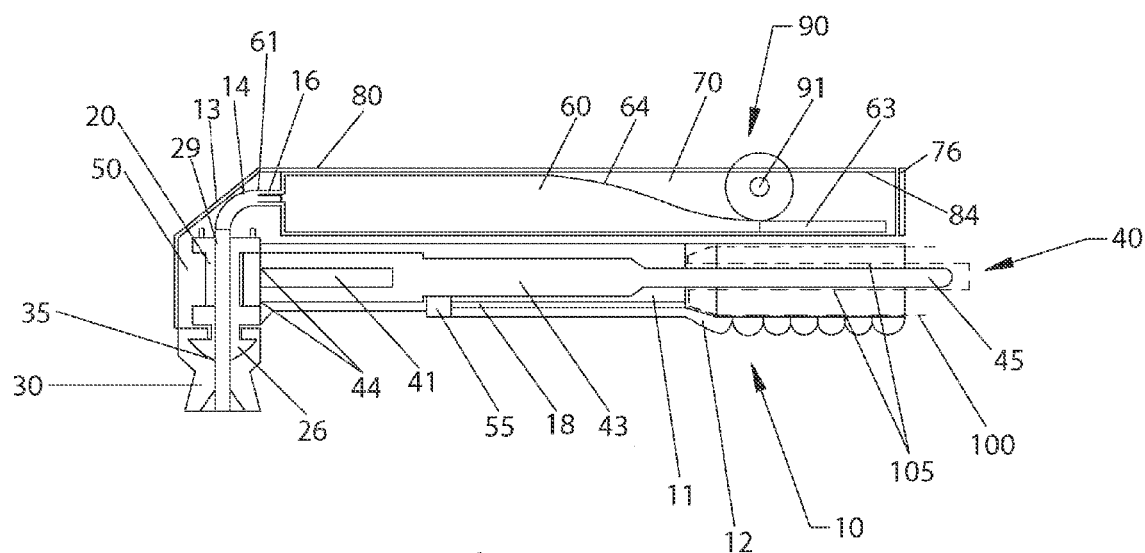
FIG. 2 is a vertical cross-sectional view showing the disposable dental instrument of the present invention.

FIG. 2 begins to illustrate elements of the present invention that overcome drawbacks of the prior art. The housing will first be described in detail to illustrate several of the novel features. The fluid container and discharge mechanism will be described afterwards.

FIG. 2 is a cross-sectional view of the present invention. A downward facing rotatable prophy cup 30 on the front end of the housing 10 is traditionally dipped into a prophylactic paste in a paste container near the instrument.

As shown, the housing 10 is a hollow tube-like passage having a central bore 11 therethrough. Extending through a long section of the central bore 11 is a drive shaft end portion 45 protruding from the back end of the housing 10. The drive shaft end portion 45 that is protruding from the back end of the housing 10 is connected to a hand motor 100 (shown in dashed outline only) that is commonly used by dentists, oral hygienists, and other dental professionals. At the opposite end of the drive shaft 40 is a drive gear 44 that meshes in geared engagement with a wheel gear 21 of a wheel 20. The central bore 11 makes a ninety degree turn at the point of geared engagement, such that the wheel 20 is at right angles to the drive shaft 40, and protrudes from the bottom of the front end of the housing 10.

The central bore 11 is wider in the back end of the housing 10 and narrower in the front end. The narrowing section 12 of the central bore 11 occurs toward the back end of the housing 10. The hand motor 100 is inserted into the central bore 11 up to the narrowing section 12 of the central bore 11. The drive shaft 40 is enclosed by a gripping surface 105 within the hand motor 100. The hand motor 100 is commonly locked into place by twisting to tighten the gripping surface 105 around the drive shaft 40. The drive shaft 40 is held securely within the housing 10 by key locking protrusion 42 extending outward perpendicular to the central bore 11 walls, preventing the drive shaft 40 from being pulled from the housing 10.

The front end of the housing 10 has an oblique head portion 13 formed with a curved drain hole 14 along the middle. The curved drain hole 14 is a passageway for movement of the tooth cleaning fluid discharged from the tube 60. Furthermore, the oblique head portion 13 has a neck portion insertion hole 16 formed at the inlet thereof for tightly fitting the tube 60 thereto.

Figure 4A:
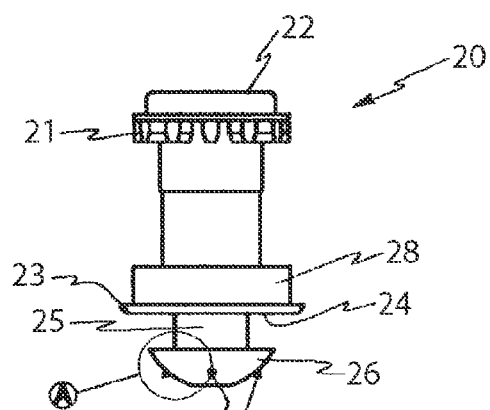
FIG. 4a is a front view showing the wheel of the disposable dental instrument of the present invention.
Figure 4B:
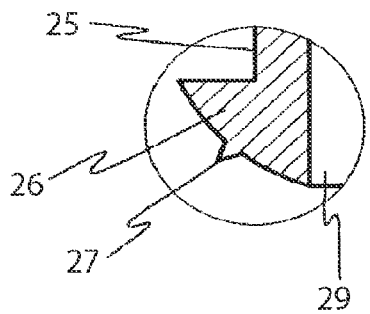
Figure 4C:
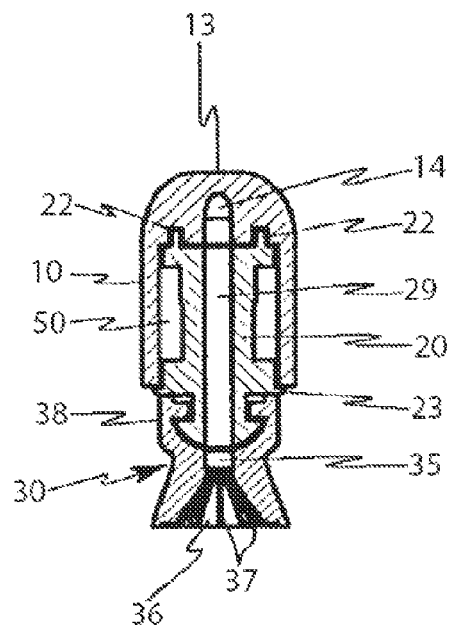
FIG. 4c is a sectional view showing the wheel assembled with the prophy cup inside the wheel room of the disposable dental instrument of the present invention.

As shown in FIG. 4a and FIG. 4c, the wheel 20 is adapted to be coupled to the wheel room 50 of the housing 10. The wheel 20 has an upwardly protruded horizontal force stabilizing ring 22 formed along the circumferential direction of the upper portion thereof in such a manner as to rub against the inner periphery of the wheel room 50, a wing ring 23 formed along the lower end portion thereof and with a relatively large peripheral surface, and a bottom face 24 adapted for tightly abutting against a close contact face 31 of the prophy cup 30.

The wheel 20 further has a relatively thin neck portion 25 formed on the lower portion of the bottom face 24 in such a manner as to be surrounded with a coupling hole 32 of the prophy cup 30 and has a generally hemispherical head portion 26 formed at the lowermost end portion thereof, the hemispherical head portion 26 having a plurality of idle preventing needles 27 formed on the peripheral surface thereof, as shown in FIG. 4b. At this time, each of the plurality of idle preventing needles 27 desirably has a protruded length of about 0.3 mm.

Figure 3A:
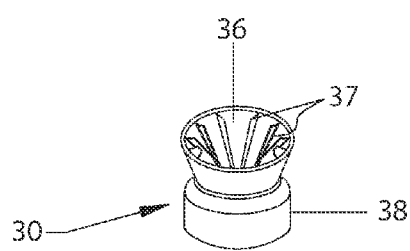
FIG. 3a is a perspective view showing the bottom portion of a prophy cup of the disposable dental instrument of the present invention.
Figure 3B:
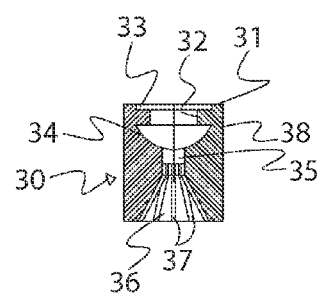
FIG. 3b is a sectional view showing the prophy cup of the disposable dental instrument of the present invention.

The prophy cup 30 that tightly abuts against the hemispherical head portion 26, the neck portion 25, and the bottom face 24 has, as shown in FIG. 3a and FIG. 3b, a close contact face 31 and a close contact groove 33 formed along the top portion thereof for enhancing the close contacting force thereof with the wheel 20 when coupled with the bottom face 24 of the wheel 20, and has a coupling hole 32 and a head-coupling portion 34 formed in the inside middle portion thereof for inserting the neck portion 25 and the hemispherical head portion 26 of the wheel 20 thereinto.

Further, the prophy cup 30 has a drain hole 35 formed to pass through the upper and down portions along the inside middle portion thereof for discharging the tooth cleaning fluid therethrough. The prophy cup 30 also has a friction space portion 36 formed at the lower portion extended from the drain hole 35 for allowing the tooth cleaning fluid supplied from the drain hole 35 to rub against the patient's tooth, and a plurality of grinding wings 37 formed at the lower portion thereof for brushing the patient's tooth, each of the plurality of grinding wings 37 having relatively larger lower face than the upper face thereof.

Figure 5:
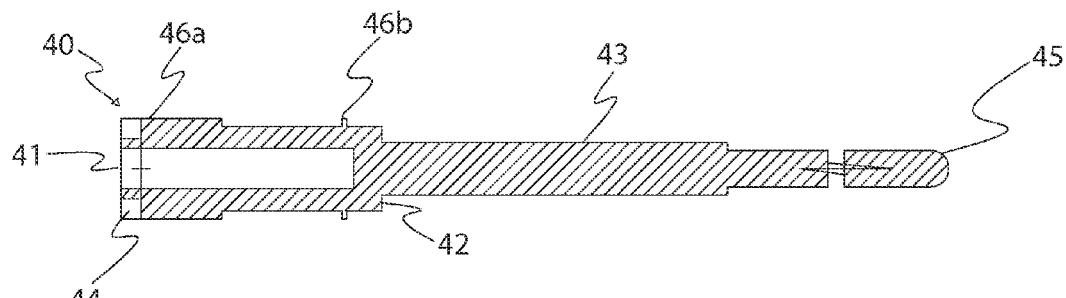
FIG. 5 is a sectional view showing a drive shaft of the disposable dental instrument of the present invention.

As shown in FIG. 5, the drive shaft 40 has a vibration-absorbing groove 41 formed in the middle portion of one side thereof for absorbing the vibration generated while it is rotated and has a drive gear 44 formed at the front end portion thereof in such a manner as to be in engagement with the wheel gear 21 of the wheel 20.

The drive shaft 40 further has a key locking protrusion 42 and a reinforcing member 43 formed stepped perpendicularly along the middle portion thereof, the reinforcing member 43 being adapted for increasing the strength of the drive shaft 40, and has two force stabilizing rings 46a and 46b formed spaced apart from each other along the outer peripheral surface thereof.

Figure 6A:
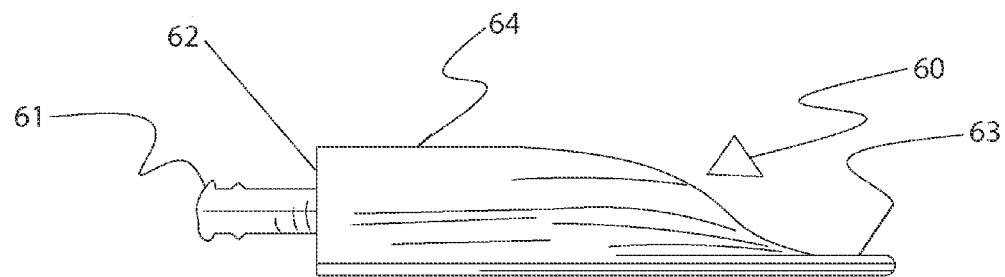
FIG. 6a is a sectional view showing a tooth cleaning fluid tube of the disposable dental instrument of the present invention.
Figure 6B:
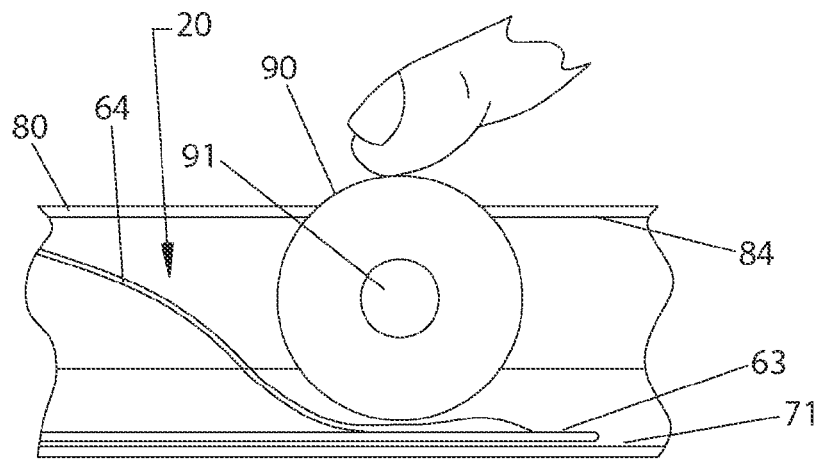
FIG. 6b is a close-up sectional view showing the roller being pressed down and forward to dispense tooth cleaning fluid from the disposable dental instrument of the present invention.
Figure 6C:
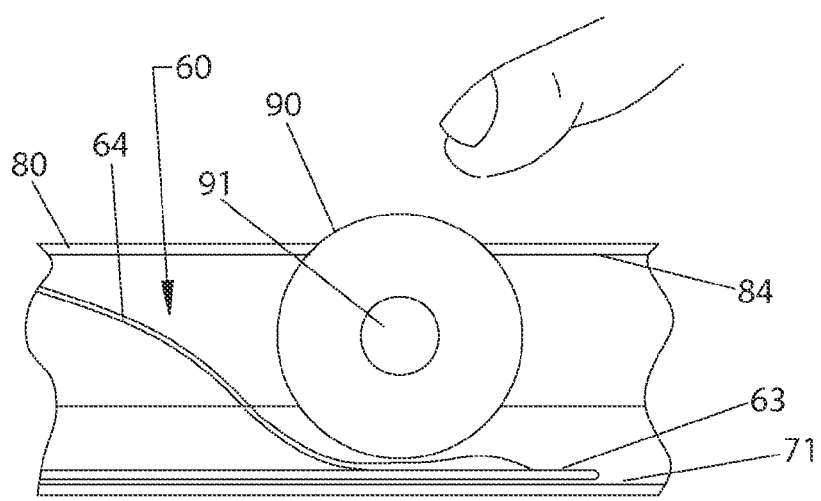
FIG. 6c is a close-up sectional view showing the roller released after being pushed forward to dispense tooth cleaning fluid from the disposable dental instrument of the present invention.

As shown on FIG. 6a, the tube 60 is a flexible bladder similar in function and form to a tube of toothpaste. The tube is composed of a flexible thermoplastic or other flexible material that allows the tube 60 to be squeezed when pressure is applied as shown on FIG. 6b. However, when the pressure is released, the tube 60 springs up as shown on FIG. 6c. The end cap 62 need not be a rigid material, so long as the end cap provides the tube inlet 61 a support surface on the tube 60. The tube inlet 61 is a small tapered lumen likely to be composed of a flexible thermoplastic or other flexible material. The tube inlet 61 is designed to fit snuggly into the neck portion insertion hole 16 of the housing 10 and still allow the tooth cleaning fluid to flow out of the tube 60 and into the neck portion insertion hole 16. At back end of the tube 60 opposite to the end cap 62, the tube 60 is pressed and heat sealed to form a slightly thicker flat surface 63.

Figure 7:
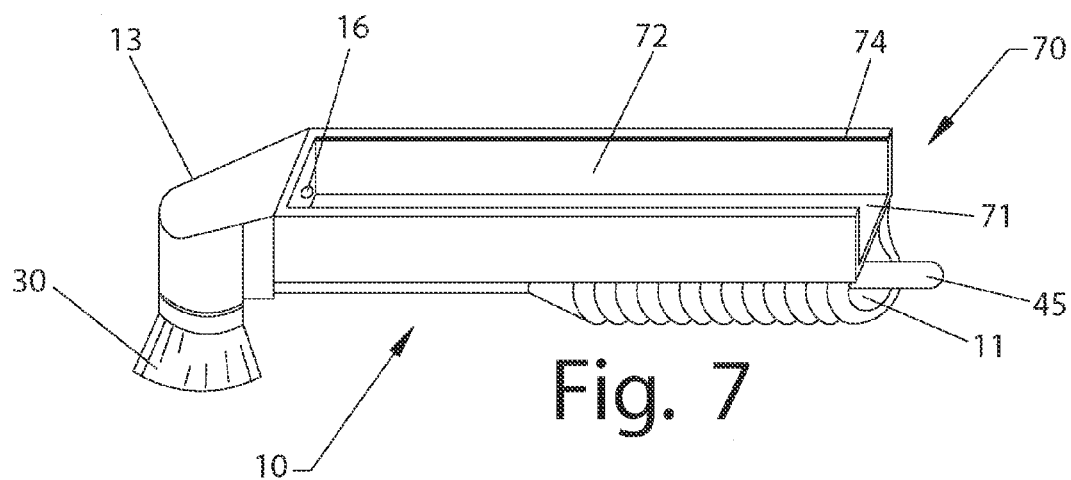
FIG. 7 is a perspective view of the housing of the disposable dental instrument of the present invention.

As shown in FIG. 7, the tube room 70 is a hollow portion located directly above the central bore 11 in the housing 10. The floor 71 of the tube room 70 is the surface on which the tube 60 is rested. At the front end of the tube room 70, the neck portion insertion hole 16 of the housing 10 is used to insert the tube inlet 61 of the tube 60 that is resting on the floor 71 of the tube room 70.

Figure 8:
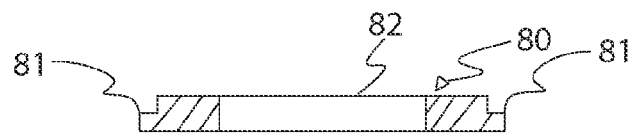
FIG. 8 is an exploded rear view of the disposable dental instrument of the present invention.
Figure 8:
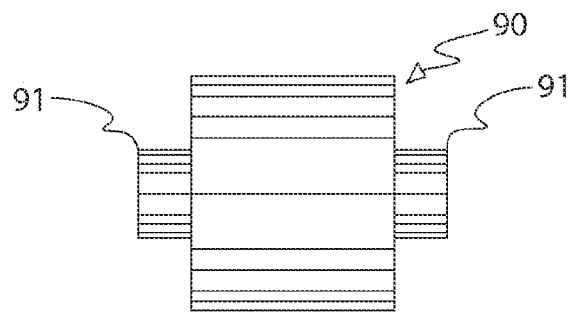
Figure 8:
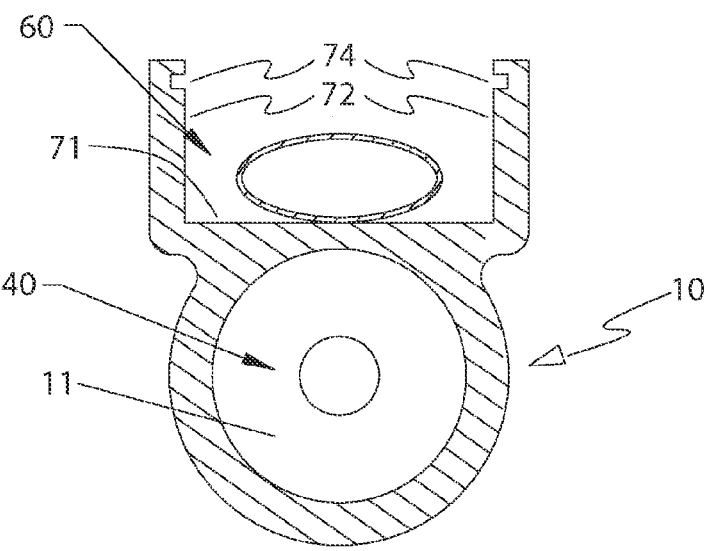

As shown in FIG. 8, the tube room sidewalls 72 extend higher than the tube 60 when filled with tooth cleaning fluid so that the tube room sidewalls 72 serve to retain the tube 60 within the tube room 70 of the dental instrument.

As shown in FIG. 8, the housing 10 has an insertion groove 74 formed at a given depth along the top of the tube room sidewalls 72 in such a manner as to be coupled with a lid 80 therealong. In essence, the tube room sidewalls 72 support the lid 80 that covers the tube room 70 so as to enclose the tube 60 within the tube room 70. Assembly of the lid 80 requires the lid 80 to be aligned with the top of the tube room sidewalls 72. As the lid 80 is evenly pressed by the application of the external force on the top surface thereof, the lid rim 81 is fitted to the insertion groove 74 of the housing 10.

A roller 90 rests within the tube room 70 and on the top surface 64 of the tube 60. The roller 90 has protrusions 91 on opposite sides that fit within the tube room sidewalls 72.

As shown in FIG. 1b, a back cover 76 can be assembled to the rear-end of the tube room 70 to improve the aesthetics of the dental instrument by covering the inside of the tube room 70 from open view. The only purpose of the back cover 76 is to improve the aesthetics of the dental instrument.

Now, an explanation of the use state of the dental instrument adapted to dispense tooth cleaning fluid to patient's teeth therefrom will be given hereinafter.

According to the present invention, the dental instrument adapted to dispense tooth cleaning fluid to a patient's teeth therefrom has the tube 60 first charged with a tooth cleaning fluid or a gel type of dentifrice material having a relatively low viscosity. Once charged, the tube 60 is securely closed by means of the tube inlet 61.

Next, the prophy cup 30 that is made of soft rubber material is coupled with the hemispherical head portion 26 of the wheel 20, and the hemispherical head portion 26 should be completely inserted into the hollow portion of the wheel room 50.

Referring to a method for coupling the prophy cup 30 with the hemispherical head portion 26 of the wheel 20, first, the hemispherical head portion 26 is pushed toward the extending head-coupling portion 34 of a hemisphere shape that is formed large in the inside middle portion of the prophy cup 30. Then, the round coupling cup 38 of the prophy cup 30 is turned to push inwardly along the peripheral surface thereof, such that the hemispherical head portion 26 is conveniently mounted into the head-coupling portion 34 and at the same time the idle preventing needles 27 are penetrated into the bottom face of the hemisphere portion of the head-coupling portion 34, which enables the prophy cup 30 to be rotated together with the wheel 20 during the rotation of the wheel 20, without having any idle.

In more detail, when the prophy cup 30 is coupled with the hemispherical head portion 26 of the wheel 20, the coupling hole 32 formed in the middle portion of the prophy cup 30 is opened to push the hemispherical head portion 26 thereinto, and at this time, even though the outer peripheral surface of the coupling cup 38 is not necessarily pressed by a finger, the prophy cup 30 is contracted by the rubber characteristics thereof such that the inner peripheral surface of the coupling hole 38 comes in close contact with the neck portion 25. At the same time, at the state where the hemispherical head portion 26 is inserted into the head-coupling portion 34 of the prophy cup 30, it is tightly fitted thereto by the contraction of the prophy cup 30 such that the ends of the idle preventing needles 27 are penetrated into the inner surface of the head-coupling portion 34. At this time, as the close contact face 31 of the prophy cup 30 comes in close contact with the bottom face 24 of the wheel 20, the prophy cup 30 can be rotated together with the wheel 20 during the rotation of the wheel 20.

Then, after the wheel 20 has been coupled with the prophy cup 30 as mentioned above, the wheel gear 21 disposed on the head portion of the wheel 20 is inserted into the wheel room 50 defined in the housing 10.

As a result, the horizontal force stabilizing ring 22 mounted along the upper peripheral surface of the wheel 20 is fitted along the force stabilizing groove 51 of a round circle shape formed on the ceiling of the wheel room 50.

Additionally, the vertical force stabilizing ring 28 comes in almost close contact along the lower inner peripheral of the wheel room 50, and the top surface of the wing ring 23 comes in almost close contact along the bottom periphery of the wheel room 50. At this state, the coupling of the wheel 20 with the drive shaft 40 is conducted.

The drive gear 44 of the front portion of the drive shaft 40 is first inserted into the central bore 11 at the back of the housing 10.

At this time, the outer peripheral surfaces of the stabilizing rings 46a and 46b of the drive shaft 40 are inserted into the central bore 11 of the housing 10 in almost close contact relation with the central bore 11, and on the other hand, the drive gear 44 is deeply inserted to be in engagement with the wheel gear 21 of the wheel 20 coupled first within the wheel room 50.

When the drive gear 44 of the drive shaft 40 that is inserted into the central bore 11 of the housing 10 are not in engagement with the wheel gear 21 of the wheel 20, one of the wheel 20 and the drive shaft 40 is somewhat rotated in left and right directions such that the drive gear 44 and the wheel gear 21 are in engagement with each other.

After the drive shaft 40 has been coupled with the wheel 20, then a stop key 55 is forcedly fitted to the rectangular key hole 17 formed along the round peripheral surface of the thin tube 18 of the housing 10.

Figure 9A:
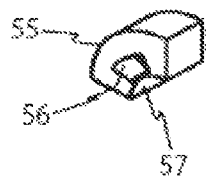
FIG. 9a is a perspective view showing a stop key of the disposable dental instrument of the present invention.
Figure 9B:
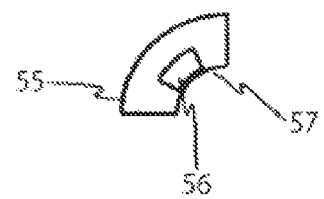

As the stop key 55, shown in FIG. 9a and FIG. 9b, is fitted to the rectangular key hole 17, a protrusion 56 is locked into the inner surface of the thin tube 18 such that the stop key 55 is not deviated from the thin tube 18, and the stop key 55 stops the key locking protrusion 42 of the drive shaft 40 at one side thereof for supporting the key locking protrusion 42 and at the same time has an inwardly curved face 57 coupled with the drive shaft 40 in such a manner as to be spaced from the drive shaft 40 by a given distance. So, since the wheel 20 is in engagement with the drive shaft 40, they are not separated from each other by the application of an external force, and also since the key locking protrusion 42 of the drive shaft 40 is locked into the stop key 55, they are not separated from each other, such that the wheel 20 and the drive shaft 40 are rigidly assembled with the housing 10.

Hereinafter, an explanation on the methods of packaging and distributing the product of the present invention, the operating states thereof, and the usage thereof will be given.

For the distribution of the product of the present invention, four parts, that is, the housing 10 assembled with the wheel 20, the prophy cup 30, and the drive shaft 40 therein by means of the stop key 55, the tube 60 charged with tooth cleaning fluid, the roller 90, and the lid 80 are assembled and packaged ready for use.

In order to use the product of the present invention, then, after the parts of the product are unpackaged, the sticker attached to the tube inlet 61 of the tube 60 is removed and the tube 60 is inserted in the tube room 70 of the housing 10.

After the tube 60 charged with tooth cleaning fluid is mounted into the tube room 70, the tube inlet 61 is fit snuggly into the neck portion insertion hole 16 of the housing 10. Then the roller 90 is placed on top of the flat surface 63 of the tube 60 located at the back end of the tube 60. The lid 80 is then aligned with the top of the tube room 70 and along the top of the tube room sidewalls 72. Finally, the lid 80 is evenly pressed by the application of the external force on the top surface thereof so that the lid rim 81 is fitted to the insertion groove 74 of the tube room 70, thereby finishing the assembling process of the disposable dental instrument according to the present invention.

If the product of the present invention is to be used for conducting dental operations, a hand motor connection reference groove 19 formed on the outer periphery of the central bore 11 of the housing 10 is disposed correspondingly at a reference protrusion of a hand motor and is then pushed fittably thereto.

Consequently, the drive shaft end portion 45 is fittably inserted into a connection hole of the hand motor 100, and at this state, if the locking mechanism of the hand motor 100 is rotated in one direction, the housing 10 is fixed to the hand motor by means of a fixing device of the hand motor 100, thereby finishing the preparation before the use of the product of the present invention.

Therefore, if a switch is turned on at a state where the hand motor is taken by the operator's hand, the hand motor 100 is rotated to rotate the drive shaft 40, and at the same time, the wheel 20 that is in perpendicular engagement with the drive shaft 40 is accordingly rotated, thereby causing the prophy cup 30 coupled with the wheel 20 to be rotated together with the wheel 20.

Next, at the state where the hand motor 100 is taken by the operator's hand, if the roller 90 is pushed forward by using his or her finger, the roller 90 applies pressure on the tube 60 that causes the tooth cleaning fluid charged therein to flow through the tube inlet 61 and toward the drain hole 29 of the wheel 20 through the curved drain hole 14 of the housing 10. The tooth cleaning fluid is then passed toward the friction space portion 36 of the prophy cup 30 through the drain hole 35 of the prophy cup 30, and it is supplied to the grinding wings 37 as the prophy cup 30 is being rotated, such that the grinding wings 37 rub against the surface of the patient's tooth.

As described in the foregoing, the disposable dental instrument according to the present invention has all parts made of synthetic resin causing no harm to a human body. The preferred embodiment is relatively small and compact in size such that it can be made in great large quantities at relatively inexpensive costs. Further, it is designed to be available easily and conveniently and is also tested with a finished product sample, such that it is found that the present invention has remarkably apparent novelty and originality when compared with the conventional practices where no embodiments have been put into practical use in the related art. Thus, the present invention can eliminate many inconveniences associated with the hand motor being turned on and off repeatedly whenever the dental operation is moved from one tooth to another tooth so as to supply the tooth cleaning material to the moved tooth.

Moreover, the product of the present invention can eliminate many inconveniences associated with removing the instrument into and from the patient's mouth repeatedly to replenish the tooth cleaning material.

Figure 10A:
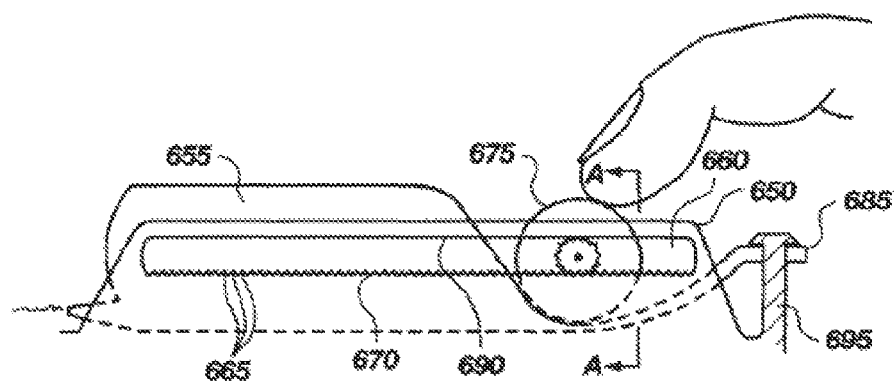
FIG. 10a is a cross-sectional view of a dental instrument of the prior art.
Figure 10B:
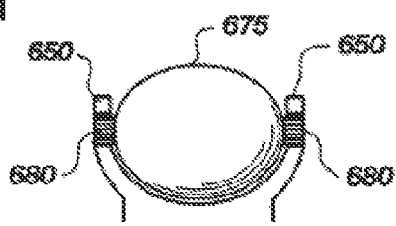

FIGS. 10*a* and 10*b* offer two views of a similar prior art system for dispensing a fluid-like agent for teeth cleaning covered by U.S. Pat. No. 2,738,528. FIG. 10*a* is a view of the simple system that the inventors believe is probably the most similar in appearance to the present invention, but which fails to accomplish the task for which it was designed. As explained previously, U.S. Pat. No. 2,738,528 shows a headpiece shelf having higher retaining walls 650 wherein the dispensing bladder 655 rests. Each retaining wall 650 has a splined slot 660 along the long axis of the shelf, the slot 660 being near the top edge of the retaining walls 650. The splines 665 are only found on the bottom edge 670 of the slot 660. An ellipsoid roller 675 rests within the shelf and retaining walls 650. The roller 675 has projections 680 on opposite sides which fit in the retaining wall slots 660 and mesh in rolling engagement with the splines 665.

The initial position of the components of the prior art has the roller 675 near the attaching end 685 of the bladder 655. A fluid agent is dispensed by pressing down and forward on the roller 675. The roller 675 acts to squeeze the fluid agent from the bladder 655. Releasing the roller 675 does not cause it to slide backwards. Instead, the roller 675 stays in position by the slight pressure of the dispensing bladder 655 slightly lifting the roller 675 causing the roller splines 665 to catch against the upper slot surface 690. The roller 675 impedes backflow of fluid agent, thus making it unnecessary to begin pushing from the now empty end of the bladder 655. The splines 665 on the lower edge 670 of the slot 660 assist the roller 675 movement by preventing roller 675 slippage, similar to a rack and pinon system.

It is noted by U.S. Pat. No. 2,738,528 that this prior art is difficult to use because of the tight space that the roller 675 must squeeze into after anchoring the bladder 655 to the securing pins 695. Furthermore, while total usable dispensing volume maybe slightly smaller than without the roller 675, fluid agent squeezed from the bladder 655 to make room for the roller 675 will not do much more than fill the passage through the headpiece to the prophy cup.

Various elements of a preferred embodiment of the present invention overcome the drawbacks of the prior art shown in FIGS. 10*a* and 10*b*, while retaining the desired simplicity of the design. First, the tube room sidewalls 72 of the present invention do not have splined slots 660 as in the prior art. Second, the roller 90 of the present invention is not ellipsoid as the roller 675 in the prior art. Third, unlike the present invention, the roller 675 of the prior art has projections 680 with splines 665 on opposite sides which fit in the retaining wall slots 660 and mesh in rolling engagement with the splines 665. Instead, the preferred embodiment of the present invention has a roller 90 with smooth protrusions 91 on opposite sides that fit within the sidewalls 72. Fourth, the roller 90 in the present invention has a serrated surface 92. Fifth, the tube 60 of the present invention does not anchor to securing pins 695 as in the prior art. Instead, a removable lid 80 is fitted to the insertion groove 74 of the housing 10 to hold the tube 60 and the roller 90 within the tube room 70. The lid slot 82 serves to guide the movement of the roller 90.

The preferred embodiment of the present invention is superior to the prior art shown on FIGS. 10*a* and 10*b* because the tube 60 is not anchored to anything, instead it has a back end opposite to the end cap 62 that is pressed and heat sealed to form a flat surface 63 on which the roller 90 is rested without any hindrance of any tight spaces as in the prior art. Secondly, the surface contact area between the roller 90 and the tube room sidewalls 72 of the preferred embodiment is the end tips 93 of the protrusions 91. The surface contact area between the roller 675 and the retaining walls 650 in the prior art, is the entire side surfaces 750 of the roller 675. By having a smaller surface contact area, the roller 90 of the preferred embodiment of the present invention is easier to control and push forward with one finger while the dental instrument is used inside a patient's mouth. Thirdly, the lid 80 of the present invention is removable and holds the tube 60 and the roller 90 in place within the tube room 70. Unlike the prior art, the lid 80 and the roller 90 can be completely and easily removed from the housing 10 to allow for a quick and easy assembly of the tube 60 into the tube room 70 of the housing 10. Finally, the serrated surface 92 of the roller 90 of the present invention is easier to manufacture and provides more control to the operator than the projections 680 with splines 720 on the roller 675 of the prior art. The serrated surface 92 prevents the roller 90 from sliding backwards when it is released by the operator. It also prevents slippage of the roller 90 and squeezes more tooth cleaning fluid from the tube 60 than a smooth surface as in the prior art.

Figure 11:
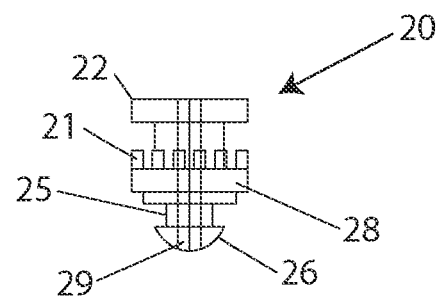
FIG. 11 is a front view of an alternative embodiment of a wheel for the dental instrument of the present invention.

FIG. 11 shows the wheel 20 in an alternative embodiment that has the wheel gear 21 on the bottom portion rather than the top portion to allow greater curvature of the curved drain hole 14 within the oblique head portion 13 of the housing 10.

The greater curvature allows better flow of the tooth cleaning fluid. With the wheel gear 21 on the bottom portion of the wheel 20, the neck portion insertion hole 16 of the housing 10 can be located at a lower position closer to the floor 71 of the tube room 70 to accommodate a tube 60 with a tube inlet 61 in the bottom portion rather than the middle portion of the tube 60.

Figure 12:
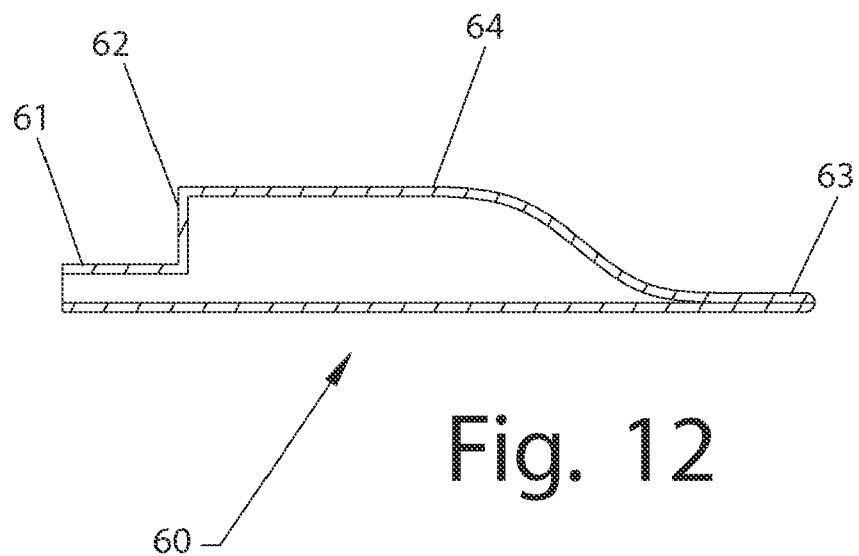
FIG. 12 is a cross-sectional view of an alternative embodiment of the tooth cleaning fluid tube of the disposable dental instrument of the present invention.

FIG. 12 shows the tube 60 in an alternative embodiment that has the tube inlet 61 at the bottom portion rather than the middle portion. Having the tube inlet 61 in the bottom portion allows more tooth cleaning fluid to be squeezed out with the roller 90.

Figure 13C:
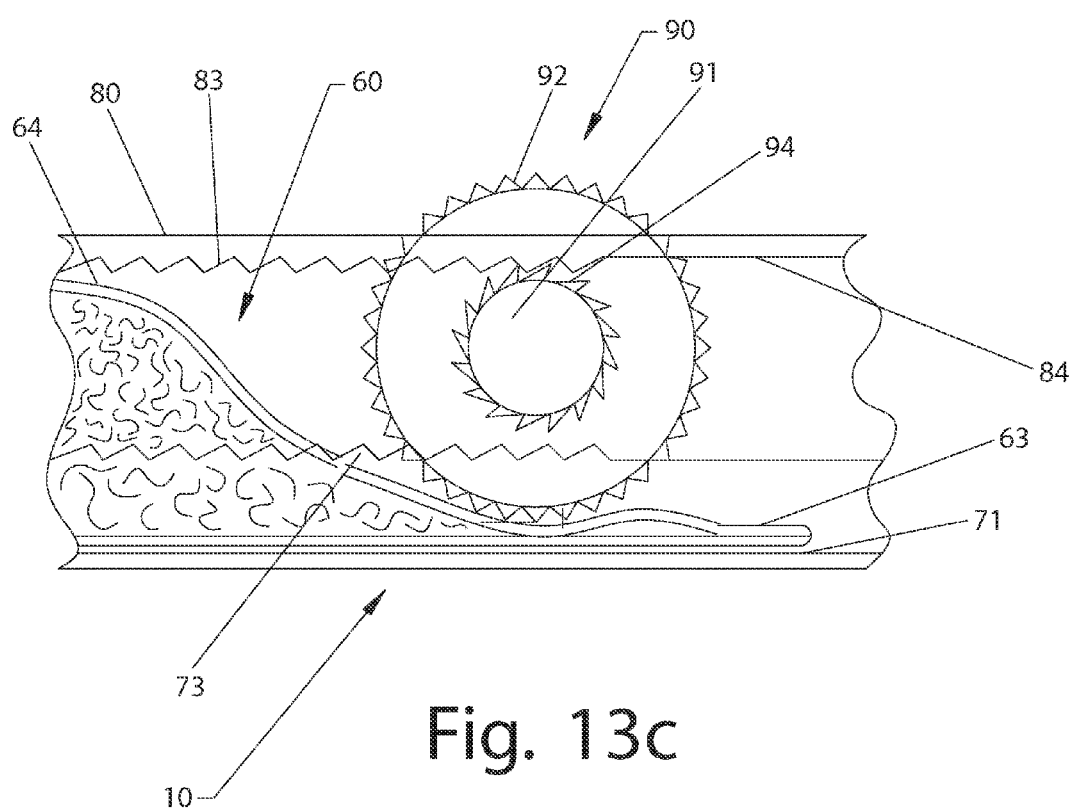
FIG. 13c is a close-up sectional view of an alternative embodiment of the roller and housing of the disposable dental instrument of the present invention.

Another alternative embodiment in shown in FIG. 13b where the inside surface 75 of the tube room sidewalls 72 have upward facing splines 73 protruding perpendicular to the inside surface 75 of the tube room sidewalls 72. The upward facing splines 73 run along the long axis of the floor 71 of the tube room 70. Then the lid 80 has downward facing splines 83 that protrude perpendicular to the bottom face 84 of the lid 80. As shown on FIG. 13a, the downward facing splines 83 is of the same length and width as the upward facing splines 73 and both run parallel facing each other when the lid 80 is assembled to the housing 10. Finally, the roller 90 has protrusions 91 on opposite sides with splines 94 that fit within the tube room sidewalls 72 and between the downward facing splines 83 and the upward facing splines 73. However, the protrusions 91 are sized and positioned so that the upward facing splines 73 and downward facing splines 83 are spaced so that the protrusions 91 mesh in rolling engagement with either the upward facing splines 73 or the downward facing splines 83 but never with both. In essence, the upward facing splines 73 guide the roller 90 in the forward direction while the downward facing splines 83 prevent the roller 90 from sliding or rolling backward. When the roller 90 is pressed down against the upward facing splines 73, it is free to move forward to squeeze tooth cleaning fluid from the tube 60. But when the roller 90 is released by the operator, the tube 60 springs up as shown in FIG. 13c and the roller 90 is pushed against the downward facing splines 83 that keeps it from sliding backwards.

Figure 14A:
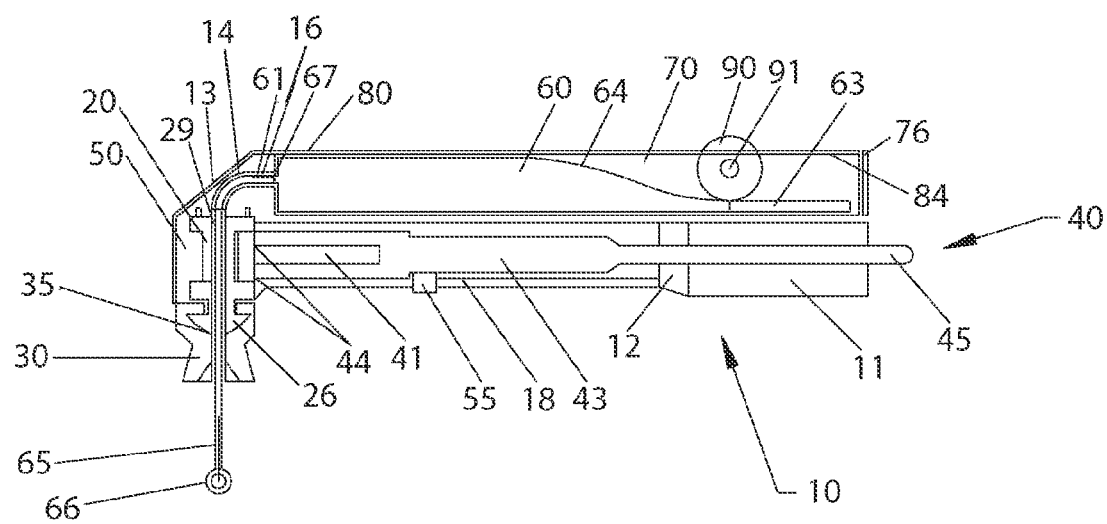
FIG. 14a is a cross-sectional view of an alternative embodiment of the disposable dental instrument of the present invention.
Figure 14B:
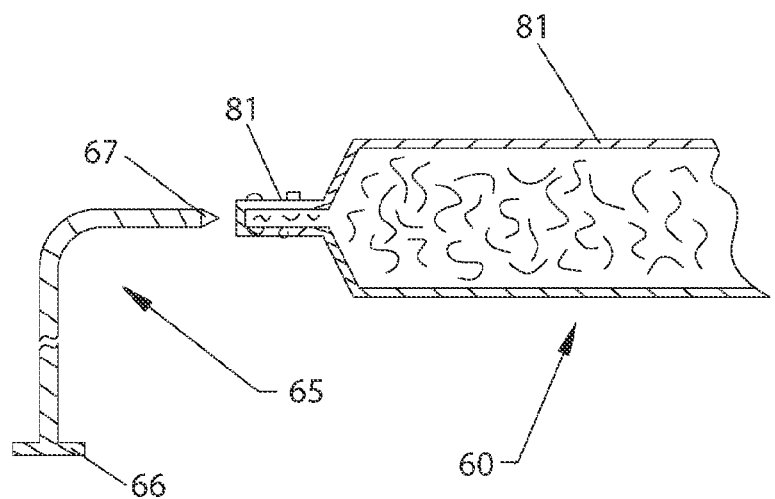
FIG. 14b is a cross-sectional view of an alternative embodiment of the tooth cleaning fluid tube of the disposable dental instrument of the present invention.

Another embodiment of the present invention is shown in FIG. 14a and FIG. 14b. The tube inlet 61 is covered with a rod 65 that is long, thin, and very flexible. The rod 65 has a pointed end tip 67 that slides into the tube inlet 61 to prevent the tooth cleaning fluid from hardening up or drying before use. On the opposite end of the pointed end tip 67, the rod 65 has a pull tab 66 that can either be molded as part of the rod 65 or that attaches to the rod 65. The pointed end tip 67 of the rod 65 is inserted into the drain hole of the prophy cup 30, through the drain hole 29 of the wheel 20, along the curved drain hole 14 of the housing 10, and into the tube inlet 61 of a tube 60 filled with tooth cleaning fluid that has been properly assembled into the tube room 70. Pulling the pull tab 66 coming out of the drain hole 35 of the prophy cup 30 would separate the pointed end tip 67 from the tube inlet 61 so that the rod 65 can be removed from the dental instrument and discarded while the tube 60 remains in place within the tube room 70 and the tube inlet 61 is unsealed so that the tooth cleaning fluid is free to flow out of the drain hole 35 of the prophy cup 30.

Figure 15A:
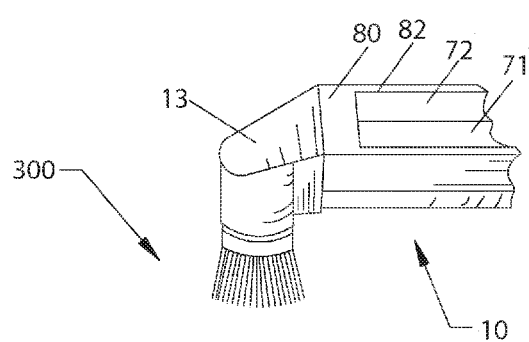
FIG. 15a is a close-up perspective view of an alternative embodiment of the prophy cup for the disposable dental instrument of the present invention.
Figure 15B:
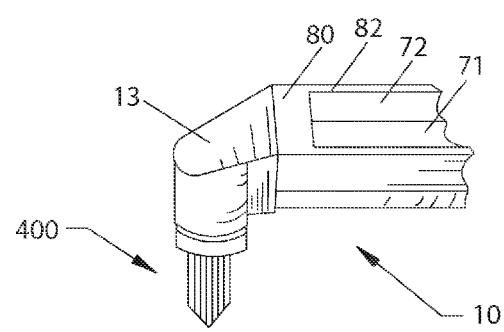
FIG. 15b is a close-up perspective view of an alternative embodiment of the prophy cup for the disposable dental instrument of the present invention.

The final embodiment of the present invention is shown in FIGS. 15a and 15b. The prophy cup is replaced with a brush head configured either as a flat brush 300 as shown in FIG. 15a or a tapered brush 400 as shown in FIG. 15b. These brush heads are ideal to clean difficult to reach areas such as areas around implants and orthodontic appliances. These brush heads are designed to be coupled with the bottom face 24 of the wheel gear 20 in the same manner as the prophy cup 30. In addition, these brush heads have a drain hole 310 and 410 formed to pass through the upper and down portions along the inside middle portion thereof for discharging the tooth cleaning fluid there through, as in the prophy cup 30.

It is to be understood that the described embodiments of the invention are illustrative only, and that modifications thereof may occur to those skilled in the art. Accordingly, this invention is not to be regarded as limited to the embodiments disclosed, but is to be limited only as defined by the appended claims herein.

What is claimed is:

1. A disposable dental instrument capable of discharging tooth cleaning fluid therefrom, comprising:

a housing having a central bore terminating in a head portion with a wheel room formed at said head portion in said housing and wherein a drain hole is formed to serve as a passageway between said wheel room and a tube room formed in said housing having inside wall surfaces with an insertion groove formed at a given depth along the top of said inside wall surfaces;

a tube composed of a flexible material mounted in said tube room and having a tube inlet that fits snuggly into said drain hole in said housing and also having flexible sidewalls that are sealed such that a planar surface is formed;

a roller having protrusions on opposite side surfaces that fit within said inside wall surfaces of said tube room;

a lid having a roller guide formed in one direction thereof being coupled therealong with said insertion groove after said tube and said roller are mounted in said tube room in such a manner as for said roller to be pushed with one finger along said roller guide to apply compressive force to said tube;

a wheel mounted in said wheel room and having a bottom face, a wheel drain hole, and a wheel gear;

a drive shaft centered and mounted for rotation within said central bore and having a shaft gear that is rotatably mounted with said wheel gear;

a prophy cup having a lower portion, a middle portion, a prophy cup drain hole formed in said prophy cup to pass through said middle portion for receiving said tooth cleaning fluid therethrough, a top periphery with a ring-shaped close contact face formed along said top periphery, an inner periphery of said ring-shaped close contact face, an elastic close contact groove formed along said inner periphery of said ring-shaped close contact face, and wherein said ring-shaped close contact face and said elastic close contact groove are adapted for close contact with said head portion of said housing and with said bottom face of said wheel; and a rod that is long, thin, and very flexible and that said rod seals said tube inlet of said tube and that said rod is inserted into said dental instrument through said prophy cup drain hole, through said wheel drain hole, through said drain hole in said housing, and into said inlet of said tube in such a manner as to unseal said inlet of said tube when said rod is pulled out of said dental instrument.

2. The disposable dental instrument according to claim 1, wherein said head portion of said housing is formed obliquely and extends downwardly at a front edge portion thereof whereby it can be inserted deeply into the patient's mouth; and wherein said drain hole in said housing is formed along a middle portion of said head portion in such a manner as to communicate with said wheel room.

3. The disposable dental instrument according to claim 1, wherein said roller has an outer serrated surface that flakes contact with said tube to prevent slippage of said roller against said tube.

4. A disposable dental instrument capable of discharging tooth cleaning fluid therefrom, comprising:
- a housing having a central bore terminating in a head portion with a wheel room formed at said head portion in said housing and wherein a drain hole is formed to serve as a passageway between said wheel room and a tube room formed in said housing having inside wall surfaces with an insertion groove formed at a given depth along the top of said inside wall surfaces and with upward facing splines formed protruding perpendicular to said inside wall surfaces at a given depth along the bottom of said inside wall surfaces;
- a tube composed of a flexible material mounted in said tube room and having a tube inlet that fits snuggly into said drain hole in said housing and also having flexible sidewalls that are sealed such that a planar surface is formed;
- a roller having protrusions with splines on opposite side surfaces that fit within said inside wall surfaces of said tube room;
- a lid having a bottom face, a roller guide formed in one direction thereof, and downward facing splines formed protruding perpendicular to said bottom face and wherein said lid is coupled therealong with said insertion groove after said tube and said roller are mounted in said tube room in such a manner as for said splines on said roller to mesh in rolling engagement with either said upward facing splines or said downward facing splines but never with both: and wherein said roller is mounted in said tube room in such a manner as for said roller to be pushed with one finger along said roller guide to apply compressive force to said tube;
- a wheel mounted in said wheel room and having a bottom face, a wheel drain hole, and a wheel gear;
- a drive shaft centered and mounted for rotation within said central bore and having a shaft gear that is rotatably mounted with said wheel gear; and
- a prophy cup having a lower portion, a middle portion, a prophy cup drain hole formed in said prophy cup to pass through said middle portion for receiving said tooth cleaning fluid therethrough, a top periphery with a ring-shaped close contact face formed along said top periphery, an inner periphery of said ring-shaped close contact face, an elastic close contact groove formed along said inner periphery of said ring-shaped close contact face, and wherein said ring-shaped close contact face and said elastic close contact groove are adapted for close contact with said head portion of said housing and with said bottom face of said wheel.

5. The disposable dental instrument according to claim 4, wherein said head portion of said housing is formed obliquely and extends downwardly at a front edge portion thereof whereby it can be inserted deeply into the patient's mouth; and wherein said drain hole in said housing is formed along a middle portion of said head portion in such a manner as to communicate with said wheel room.

6. The disposable dental instrument according to claim 4, wherein said roller has an outer serrated surface that makes contact with said tube to prevent slippage of said roller against said tube.

7. The disposable dental instrument according to claim 4, wherein said tube inlet of said tube is sealed with a rod that is long, thin, and very flexible and wherein said rod is inserted into said dental instrument through said prophy cup drain hole, through said wheel drain hole, through said drain hole in said housing, and into said inlet of said tube in such a manner as to unseal said inlet of said tube when said rod is pulled out of said dental instrument.

8. A disposable dental instrument capable of discharging tooth cleaning fluid therefrom, comprising:
- a housing having a central bore terminating in a head portion with a wheel room formed at said head portion in said housing and wherein a drain hole is formed to serve as a passageway between said wheel room and a tube room formed in said housing having inside wall surfaces with an insertion groove formed at a given depth along the top of said inside wall surfaces;
- a tube composed of a flexible material mounted in said tube room and having a tube inlet that fits snuggly into said drain hole in said housing and also having flexible sidewalls that are sealed such that a planar surface is formed;
- a roller having protrusions on opposite side surfaces that fit within said inside wall surfaces of said tube room;
- a lid having a roller guide formed in one direction thereof being coupled therealong with said insertion groove after said tube and said roller are mounted in said tube room in such a manner as for said roller to be pushed with one finger along said roller guide to apply compressive force to said tube;
- a wheel mounted in said wheel room and having a bottom face, a wheel drain hole, and a wheel gear;
- a drive shaft centered and mounted for rotation within said central bore and having a shaft gear that is rotatably mounted with said wheel gear;
- a brush head having a lower portion, a middle portion, a brush head drain hole formed in said brush head to pass through said middle portion for receiving said tooth cleaning fluid therethrough, a top periphery with a ring-shaped close contact face formed along said top periphery, an inner periphery of said ring-shaped close contact face, an elastic close contact groove formed along said inner periphery of said ring-shaped close contact face, and wherein said ring-shaped close contact face and said elastic close contact groove are adapted for close contact with said head portion of said housing and with said bottom face of said wheel; and
- a rod that is long, thin, and very flexible and that said rod seals said tube inlet of said tube and that said rod is inserted into said dental instrument through said prophy cup drain hole, through said wheel drain hole, through said drain hole in said housing, and into said inlet of said tube in such a manner as to unseal said inlet of said tube when said rod is pulled out of said dental instrument.

9. The disposable dental instrument according to claim 8, wherein said head portion of said housing is formed obliquely and extends downwardly at a front edge portion thereof whereby it can be inserted deeply into the patient's mouth; and wherein said drain hole in said housing is formed along a middle portion of said head portion in such a manner as to communicate with said wheel room.

10. The disposable dental instrument according to claim 8, wherein said roller has an outer serrated surface that makes contact with said tube to prevent slippage of said roller against said tube.

11. A disposable dental instrument capable of discharging tooth cleaning fluid therefrom, comprising:
- a housing having a central bore terminating in a head portion with a wheel room formed at said head portion in said housing and wherein a drain hole is formed to serve as a passageway between said wheel room and a tithe room formed in said housing having inside wall surfaces with an insertion groove formed at a given depth along the top of said inside wall surfaces and with upward facing splines formed protruding perpendicular to said inside wall surfaces at a given depth along the bottom of said inside wail surfaces;

a tube composed of a flexible material mounted in said tube room and having a tube inlet that fits snuggly into said drain hole in said housing and also having flexible sidewalls that are sealed such that a planar surface is formed;

a roller having protrusions with splines on opposite side surfaces that fit within said inside, wall surfaces of said tube room;

a lid having a bottom face, a roller guide formed in one direction thereof, and downward facing splines formed protruding perpendicular to said bottom face; and wherein said lid is coupled therealong with said insertion groove after said tube and said roller are mounted in said tube room in such a manner as for said splines on said roller to mesh in rolling engagement with either said upward facing splines or said downward facing splines but never with both; and wherein said roller is mounted in said tube room in such a manner as for said roller to be pushed with one finger along said roller guide to apply compressive force to said tube;

a wheel mounted in said wheel room and having a bottom face, a wheel drain hole, and a wheel gear;

a drive shaft centered and mounted for rotation within said central bore and having a shaft gear that is rotatably mounted with said wheel gear; and a brush head having a lower portion, a middle portion, a brush head drain hole formed in said brush head to pass through said middle portion for receiving said tooth cleaning fluid therethrough, a top periphery with a ring-shaped close contact face formed along said top periphery, an inner periphery of said ring-shaped close contact face, an elastic close contact groove formed along said inner periphery of said ring-shaped close contact face, and wherein said ring-shaped close contact face and said elastic close contact groove are adapted for close contact with said head portion of said housing and with said bottom face of said wheel.

12. The disposable dental instrument according to claim 11, wherein said head portion of said housing is formed obliquely and extends downwardly at a front edge portion thereof whereby it can he inserted deeply into the patient's mouth; and wherein said drain hole in said housing is formed along a middle portion of said head portion in such a manner as to communicate with said wheel room.

13. The disposable dental instrument according to claim 11, wherein said roller has an outer serrated surface that makes contact with said tube to prevent slippage of said roller against said tube.

14. The disposable dental instrument according to claim 11, wherein said tube inlet of said tube is sealed with a rod that is long, thin, and very flexible and wherein said rod is inserted into said dental instrument through said brush head drain hole, through said wheel drain hole, through said drain hole in said housing, and into said inlet of said tube in such a manner as to unseal said inlet of said tube when said rod is pulled out of said dental instrument.

* * * * *